United States Patent [19]

Prince

[11] Patent Number: 5,304,228
[45] Date of Patent: Apr. 19, 1994

[54] METHOD FOR MAKING OPTICAL FIBER WITH ATRAUMATIC ROUNDED END FOR USE IN LASER ANGIOPLASTY

[76] Inventor: Martin R. Prince, 71 Fulkerson St. #306, Cambridge, Mass. 02141

[21] Appl. No.: 919,150

[22] Filed: Jul. 23, 1992

Related U.S. Application Data

[62] Division of Ser. No. 484,181, Feb. 23, 1990, Pat. No. 5,133,709.

[51] Int. Cl.⁵ ............................................ C03B 37/023
[52] U.S. Cl. ...................................... 65/3.11; 65/4.2; 65/37; 65/109; 65/120
[58] Field of Search ................ 65/3.11, 3.4, 37, 57, 65/109, 120, 4.2, 4.21

[56] References Cited

U.S. PATENT DOCUMENTS

| | | | |
|---|---|---|---|
| 3,263,852 | 8/1966 | Fridrich | 65/109 X |
| 3,843,865 | 10/1974 | Nath | 219/121.6 |
| 4,118,270 | 10/1978 | Pan et al. | 156/659 |
| 4,163,601 | 8/1979 | Olshansky | 65/3.11 X |
| 4,182,787 | 1/1980 | Goossens et al. | 428/36 |
| 4,398,790 | 8/1983 | Righini et al. | |
| 4,648,892 | 3/1987 | Kittrell et al. | 65/4.21 |
| 4,678,268 | 7/1987 | Russo et al. | |
| 4,693,556 | 9/1987 | McCaughan | |
| 4,729,621 | 3/1988 | Edelman | |
| 4,844,580 | 7/1989 | Lynch et al. | |
| 4,898,450 | 2/1990 | Jannson et al. | |
| 4,944,567 | 7/1990 | Kuper et al. | |

FOREIGN PATENT DOCUMENTS 2210560 6/1989 United Kingdom ................ 606/7

Primary Examiner—Robert L. Lindsay
Attorney, Agent, or Firm—Richard J. Birch

[57] ABSTRACT

An apparatus for delivery of high intensity laser radiation of large spot size into arteries and a method for making same are disclosed. An optical radiating apparatus is formed on one end of a light-conducting optical fiber such that high intensity laser radiation leaves the optical radiation apparatus with a spot size that is expanded to a diameter significantly larger than the optical fiber diameter. The apparatus comprises a small diameter, flexible fiber which tapers to a large diameter, smooth, rounded ball tip. The taper allows the beam to expand to several millimeters in diameter and thereby ablate a large channel through an occluded artery. The smooth ball tip minimizes the chance of mechanical dissection or performation. The fiber material is continuous such that there are no optical interfaces. The light radiation apparatus is manufactured to ensure uniformity of light intensity and the ability to transmit intense light without developing regions of mechanical, thermal or optical damage to the apparatus.

11 Claims, 1 Drawing Sheet

METHOD FOR MAKING OPTICAL FIBER WITH ATRAUMATIC ROUNDED END FOR USE IN LASER ANGIOPLASTY

This is a divisional of copending application(s) Ser. No. 07/484,181 filed on Feb. 23, 1990 now U.S. Pat. No. 5,133,709.

The present invention relates to fiber optic devices and method of manufacturing said devices and more particularly to a device for dispersing light propagating along an optical fiber into a uniform pattern illuminating the majority of the forward surface of a ball-tipped fiber.

BACKGROUND AND PRIOR ART

Laser angioplasty is a promising method of opening arteries that are obstructed by atherosclerotic plaque. It has many potential advantages over surgery, balloon angioplasty and other forms of vascular interventions. Laser radiation may be introduced into arteries via small optical fibers, thus avoiding major surgery; the radiation can remove plaque rather than merely pushing it aside, thus, potentially reducing the high rate of restenosis that occurs with balloon angioplasty; radiation has the potential to be absorbed preferentially by plaque, thereby adding an element of specificity and safety that may not exist with mechanical atherectomy devices; and finally, the laser can remove tissue in fine increments, much smaller than what can be removed mechanically.

Early laser angioplasty systems, however, have not taken full advantage of the unique properties of laser radiation. As a result, there have been frequent perforations, dissections and other problems associated with inadvertent damage to the underlying normal artery wall. This inadvertent damage can be categorized into laser tissue interaction problems and laser delivery system problems.

Many of the laser-tissue interaction problems are now solved by careful selection of laser parameters. The massive thermal injury that occurred with continuous wave lasers can be minimized by using pulse durations that are short compared to the tissue thermal relaxation time. (Anderson R. R., Parrish J. A., "Selective Photothermolysis: Precise Microsurgery by Selective Absorption of Pulsed Radiation," Science 220:524-527, 1983.) Calcified plaque, which could not be removed with low to moderate intensity lasers, is now known to be readily plasma-ablated with high intensity radiation. (Prince M.R., et. al., "Selective Ablation of Calcified Arterial Plaque with Laser-Induced Plasmas." IEEE J. Quantum Electronics QE23:1783-6, 1987.) Specificity for plaque (frequently called selective ablation) is achieved by choosing a wavelength where plaque absorption is much greater than normal artery absorption. (Prince M.R., et. al., "Selective Laser Ablation of Atheromas Using a Flashlamp-Excited Dye Laser at 465 nm., Proc. Nat. Acad. Sci. USA 83:7064-8, 1986.) Fine, "precise" ablation is achieved at wavelengths where plaque absorption is strong or can be enhanced with exogenous chromophores.

Laser delivery problems, however, have been more difficult to resolve. The bare fibers that were used initially have been shown to have sharp edges which readily perforate arteries like a needle even when the laser is not turned on. (Sanborn et al., "Percutaneous Coronary Laser Thermal Angioplasty", Journal of American College of Cardiology 1986:8, 1437-1440) with their "hot tip" fiber, have eliminated the sharp end by covering the optical fiber with a rounded, metal cap. This rounded, bulbous cap allows the fiber to track well down arterial lumens and avoid mechanical perforation, but it forgoes many advantages of having laser radiation reach the tissue. Some investigators have melted the end of the fiber to form a ball with a similar shape as the "hot tip". This retains the desirable shape but allows all of the laser radiation to reach the tissue. Unfortunately, the laser beam spot size tends to be much smaller than the ball diameter and the tip tends to be fragile, thus creating the risk of embolizing the tip. Some of these problems have been overcome by mouting a transparent rounded window a fixed distance from the end of the fiber. Using a steel coupler, the window can be firmly attached thus avoiding the possibility of embolization. The space between the window surface and the fiber tip allows the laser beam to expand sufficiently to whatever diameter is desired. However, the window has several problems: the dead space may accumulate blood; there is a long bulky stiff end; and the extra interfaces create some loss of energy that makes it difficult to transmit enough high intensity radiation to effectively ablate material, especially calcified plaque. A fiber optic with a convex surface to change the output pattern of radiation is described by Righini in U.S. Pat. No. 4,398,790.

Ball-tipped fibers have been described in other branches of medicine also. McCaughan, in U.S. Pat. No. 4,693,556, describes a ball-tipped optical fiber for producing a spherical pattern of light. The McCaughan device is unsuitable for laser angioplasty because the energy radiates in all directions instead of forward, toward the obstructing plaque. This device is suitable for delivery of low intensity light (less than 100 watts) as the described device can not withstand the intense radiation (of the order of kilowatts to megawatts) required for pulsed, selective laser angioplasty. In addition, the McCaughan device still has an unsupported tip which can break.

It is, accordingly, a general object of this invention to provide an improved optical delivery device for laser angioplasty with a smooth, rounded, atraumatic, "lumen-seeking" tip with a large spot size, no optical interfaces within the fiber, the ability to accept intense radiation and a short still end.

SUMMARY AND OBJECTS OF THE INVENTION

The present invention discloses an optical radiating apparatus constructed on one end of a light-conducting optical fiber such that, upon encountering this radiator, light is caused to leave the fiber and radiate from the fiber in a nearly uniform pattern.

The present invention describes an apparatus with a short, stiff end for improved maneuverability.

The present invention describes an apparatus with an atraumatic, rounded shape which limits the risk of perforation and tracks the lumen of the artery.

The present invention describes a taper of specific size leading to the ball-tip which provides for an enlarged irradiation area.

The present invention describes a radio-opaque reinforcement piece which provides added strength to the tip, added steerability, and adds the ability to image the fiber tip under direct fluoroscopy.

The present invention describes a buffer material over the reinforcement piece which adds maneuverability and steerability, and maintains the integrity of the apparatus if the fiber is broken.

The present invention provides a method of manufacturing the optical fiber with the properties described in a reliable and reproducible fashion, without having to alter the speed of fiber drawing equipment.

DESCRIPTION OF THE PREFERRED EMBODIMENTS

Figure 1:
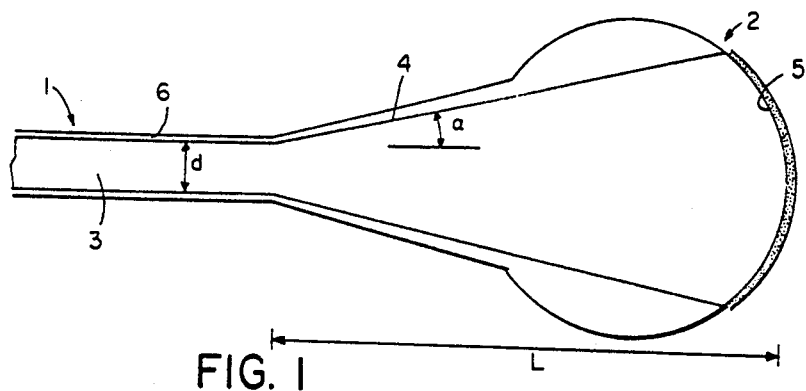
FIG. 1 is a diagrammatic view in side elevation showing the optical radiating apparatus on the tip of an optical fiber.

FIG. 1 shows in side view an optical fiber, 1 conducting light from the left portion of the figure into the region of an optical radiating tip, 2. The optical radiating tip is composed of fiber material which has been altered through a series of operations described below. The radiating rounded end portion or "ball-tip," 2, is typically small enough to insert into a patient, frequently through a catheter inserted into the leg or arm, where the tip can be advanced to an area of occlusive cardiovascular disease or where high intensity radiation can have a positive therapeutic effect. On occasion, the tip can be inserted through a surgical incision, in which case the outer dimension of the tip can be larger. Another property of the radiating apparatus is its ability to withstand the high intensity laser radiation. At 480 nanometers, the fiber 1 and its optical indicating tip 2 withstand peak powers of up to 40 MegaWatts per centimeter squared ($cm^2$).

Figure 2:
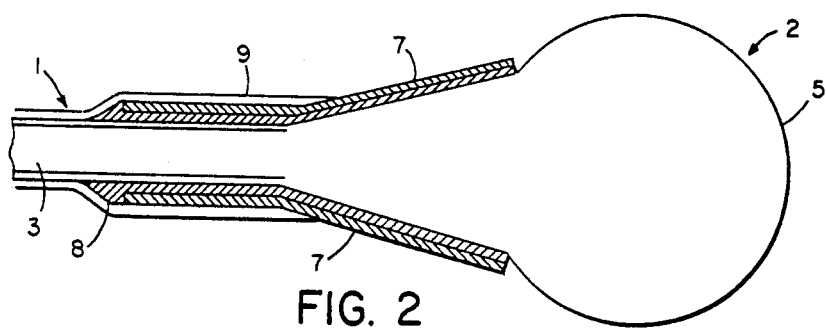
FIG. 2 is a diagrammatic view in side elevation showing the tip portion of the optical radiating apparatus with reinforcement and sheathing materials; and, FIGS. 3 through 6 illustrate the steps in making the optical radiating apparatus
Figure 3:
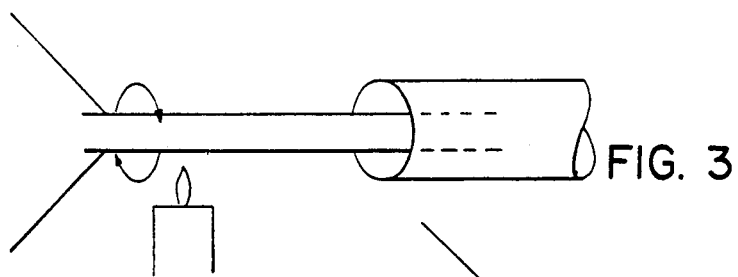
Figure 4:
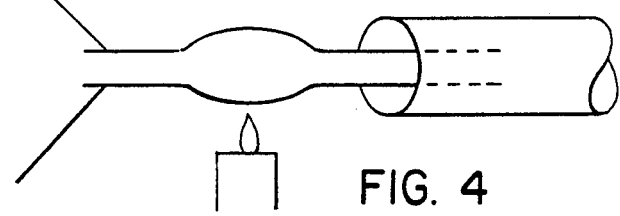
Figure 5:
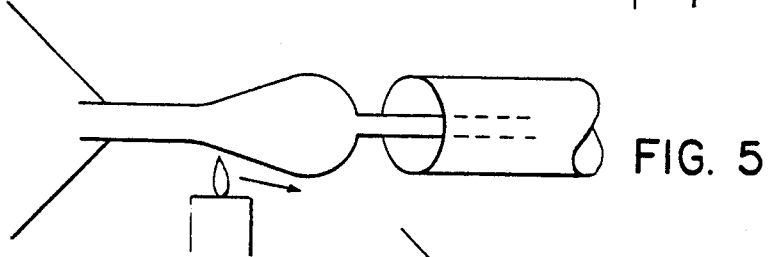
Figure 6:
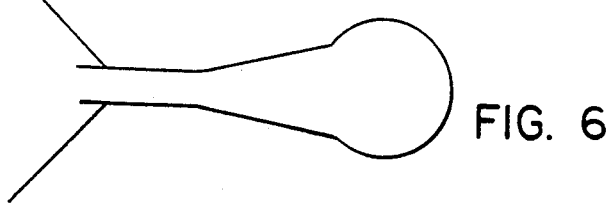

FIG. 2 shows in side view the optical fiber terminating in radiating tip 2. The fiber light carrying core 3 enlarges into a taper position 4 and then into the rounded end portion 5. Materials 3, 4, and 5 are comprised of the same optical carrying material. The angle, alpha, of the taper portion 4 is defined so that the divergence angle of the light being emitted from the fiber is contained within the angle of the light. The divergence angle differs depending on the fiber material being employed. The "ball-tipped" region varies in size from as small as one millimeter to as large as six millimeters in diameter.

One of the objective of the invention is to provide that most of the forward surface of the "ball-tip" 2 is illuminated with uniform laser radiation. The precise area illuminated is complex because of the curved ball surface. However, using geometrical optics, the radiation spot size on a plane perpendicular to the fiber at its tip is given by the following equation.

$$\text{Spot Size} = d + 2L\,{}^*(N.A./N_f)$$

Where
d = fiber core 3 diameter
L = Length from beginning of taper to end of ball
N.A. = fiber numerical aperture
Nf = fiber core index of refraction The invention allows the angle (as measured from the optical axis of the fiber; angle alpha in FIG. 1) of the taper portion 4 to be sufficient to permit maximal beam expansion (i.e. $>\sin^{-1}(N.A./N_f)$. This spot size may become marginally smaller as the light penetrates into the tissue because of the focusing effect of the curved ball surface. However, in a saline environment, the index mismatch at the surface will be small and the depth of penetration of the light will be small, so this effect will be negligible. If scattering is significant, scattering may enlarge the calculated spot size.

By using different fiber numerical apertures and diameters one can achieve any spot size with even very short taper lengths. In practice, the best fibers for high intensity visible radiation have a quartz core (Nf = 1.46) and a doped quartz cladding to give a numerical aperture of about 0.22. For most applications, one also needs to keep the diameter, d, small to have adequate flexibility. Using a 200 micron fiber with a numerical aperture of 0.22 and a taper length of 1 mm, the spot size will be 0.5 $mm^2$. A 600 micron fiber with a 10 mm taper will have a spot size of 3.6 $mm^2$.

The optical fiber 3 is covered with cladding material 6, which has a relatively low index of refraction compared to the refraction index of the optical fiber 3. A radio-opaque sleeve 7 with a high tensile strength surrounds the fiber 3 and taper portion 4. One material with good strength is stainless steel, which is not only readily visible under fluoroscopy but also provides structural support for the fiber tip. The radio-opaque material may be mechanically crimped onto the fiber or affixed via a biocompatible epoxy material 8.

The fiber 3 and its taper portion 4, and radio-opaque sleeve 7 are covered with a thin tube of plastic material 9. The properties of this material are that it covers the stainless steel sleeve, provides a smooth, biocompatible, nonthrombogenic surface to facilitate manipulations through catheters and minimizes clot formation on the fiber surface. One suitable material for this coating is teflon. A teflon covered, 400 micron fiber is similar in diameter and flexibility to a 0.035 inch guidewire. By passing catheters coaxially over the fiber it is possible to steer the tip with a curved catheter or to inject fluid near the tip, i.e. saline to displace blood or contrast to allow fluoroscopic visualization of the lumen.

The most difficult part of manufacturing the optical radiating apparatus is the formation of its taper portion 4. Normally, heating a fiber end will always form a ball without a taper due to the strong surface tension of molten quartz in air. When fibers are made by drawing from a large diameter boule of quartz, the fiber diameter is determined in part by the rate of pulling on the fiber. Thus, the fiber diameter can be varied by changing the rate of pulling during fiber drawing. This, however, produces an unpredictable taper length and is prohibitively expensive.

An alternative, less expensive and more predictable method is to mount the fiber on a lathe and gradually heat a mid-section of the fiber with a torch, such as an oxy-methane flame. As the fiber softens and becomes molten, surface tension will cause the fiber to slowly increase in diameter in the molten region. By moving the flame down the fiber, a taper of any shape and length can be formed. Even more precise heating of the fiber can be obtained by using a carbon dioxide laser instead of a torch. Once the taper is formed, any fiber remaining at the end can be broken off and discarded or melted to form a large rounded end.

Any melted region of the fiber can be flame annealed and then reclad by dipping the fiber into a low index polyimide cladding material. A stainless steel sleeve with a tapered end can be glued on with biocompatible epoxy and the fiber/sleeve covered with heat shrink teflon tubing.

Having described in detail a preferred embodiment of my invention, it will be apparent to those skilled in the art that various modifications can be made therein without departing from the scope of the invention as described in the appending claims:

What I claim is:

1. A method for manufacturing an optical fiber having a relatively uniform rounded end portion with a taper portion formed between the fiber and the rounded end, so that radiation can be irradiated at an area on the rounded end portion that is approximately equal to the diameter of the core of the optical fiber plus two times the length of the taper portion times the numerical aperture divided by the optical fiber core index of refraction, said method comprising the steps of:
   (a) mounting an optical fiber on lathe;
   (b) heating the optical fiber to a high enough temperature to cause the fiber to begin to melt while turning the lathe at a high enough speed to provide for uniform heating;
   (c) continuing the heating for a long enough period to cause the natural surface tension to expand the diameter of the optical fiber;
   (d) moving the source of heat along the longitudinal axis of the optical fiber to form the desired taper shape and length; and,
   (e) heating of the taper end of the optical fiber to form a round end portion of the desired diameter.

2. A method for manufacturing an optical fiber having a rounded end with a taper portion formed between the fiber and the rounded end so that radiation can be irradiated at an area on the rounded end portion that is approximately equal to the diameter of the core of the optical fiber plus two times the length of the taper portion times the numerical aperture divided by the optical fiber core index of refraction, said method comprising the steps of:
   (a) heating a mid-portion of the fiber for a long enough period of time to allow the natural surface tension of the fiber to expand the fiber diameter, thereby forming a bulge in the fiber in the region being heated said heating occurring while rotating the fiber;
   (b) moving the source of the heat along the longitudinal axis of the optical fiber to expand the bulge into the desired taper shape and length; and,
   (c) heating the end of the optical fiber to form a rounded end portion of the desired diameter, adjoining the taper.

3. The method of claim 2 wherein the heat source is a laser.

4. The method of claim 2 wherein the heat source is an oxygen-methane torch flame.

5. The method of claim 2 wherein the heat source is an oxygen-acetylene torch flame.

6. The method of claim 2 wherein the heat source is an electrical element.

7. The method of claim 2 wherein the fiber is rotated on a lathe to provide for uniform radial heating.

8. The method of claim 3 wherein the fiber is rotated on a lathe to provide for uniform radial heating.

9. The method of claim 4 wherein the fiber is rotated on a lathe to provide for uniform radial heating.

10. The method of claim 5 wherein the fiber is rotated on a lathe to provide for uniform radial heating.

11. The method of claim 6 wherein the fiber is rotated on a lathe to provide for uniform radial heating.

* * * * *